(12) United States Patent
Chaudhary et al.

(10) Patent No.: US 10,238,107 B2
(45) Date of Patent: *Mar. 26, 2019

(54) ANTI-ADHERENT COMPOSITION

(71) Applicant: KIMBERLY-CLARK WORLDWIDE, INC., Neenah, WI (US)

(72) Inventors: Vinod Chaudhary, Appleton, WI (US); Kathleen C. Engelbrecht, Kaukauna, WI (US); David W. Koenig, Menasha, WI (US); Divesh Bhatt, Marietta, GA (US); Amy L. Vanden Heuvel, Hortonville, WI (US); Scott W. Wenzel, Neenah, WI (US); Stacy A. Mundschau, Weyauwega, WI (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/329,653

(22) PCT Filed: Apr. 1, 2015

(86) PCT No.: PCT/US2015/023817
§ 371 (c)(1),
(2) Date: Jan. 27, 2017

(87) PCT Pub. No.: WO2016/018474
PCT Pub. Date: Feb. 4, 2016

(65) Prior Publication Data
US 2017/0208798 A1    Jul. 27, 2017

Related U.S. Application Data

(60) Provisional application No. 62/031,687, filed on Jul. 31, 2014.

(51) Int. Cl.
*A01N 31/02* (2006.01)
*A01N 25/02* (2006.01)
(Continued)

(52) U.S. Cl.
CPC ............ *A01N 31/02* (2013.01); *A01N 25/02* (2013.01); *A01N 25/08* (2013.01); *A01N 37/44* (2013.01); *A01N 41/08* (2013.01); *A01N 43/36* (2013.01); *A01N 45/00* (2013.01); *A01N 47/20* (2013.01); *A01N 55/00* (2013.01); *A01N 63/02* (2013.01); *A01N 65/00* (2013.01); *A61K 8/0208* (2013.01); *A61K 8/8152* (2013.01);
(Continued)

(58) Field of Classification Search
CPC ........ A01N 31/02; A01N 25/08; A01N 25/02; A01N 47/20; A01N 55/00; A01N 41/08; A01N 63/02; A01N 37/44; A01N 65/00; A01N 43/36; A01N 65/12; A01N 45/00
See application file for complete search history.

(56) References Cited

U.S. PATENT DOCUMENTS 3,338,992 A    8/1967 Kinney
3,341,394 A    9/1967 Kinney
(Continued)

FOREIGN PATENT DOCUMENTS

CN    102784079 A    11/2012
CN    103387894 A    11/2013
(Continued)

OTHER PUBLICATIONS

Katsikogianni, M. and Y.F. Missirlis, "Concise Review of Mechanisms of Bacterial Adhesion to Biomaterials and of Techniques Used in Estimating Bacteria-Material Interactions," European Cells and Materials, vol. 8, University of Patras, Patras, Greece, Dec. 2004, pp. 37-57.
Co-pending U.S. Appl. No. 15/521,468, filed Apr. 24, 2017, by Koenig et al. for "Anti-Adherent Bontanical Compositions."
Co-pending U.S. Appl. No. 15/329,799, filed Jan. 27, 2017, by Engelbrecht et al. for "Anti-Adherent Composition."
Co-pending U.S. Appl. No. 15/500,671, filed Jan. 31, 2017, by Chaudhary et al. for "Anti-Adherent Alcohol-Based Composition."
Co-pending U.S. Appl. No. 15/329,611, filed Jan. 27, 2017, by Engelbrecht et al. for "Anti-Adherent Composition."

*Primary Examiner* — Doan T Phan
(74) *Attorney, Agent, or Firm* — Kimberly-Clark Worldwide, Inc.

(57) ABSTRACT

Compositions for inhibiting the attachment of microbes to a biotic or abiotic surface are disclosed. The compositions include a carrier and an effective amount of an anti-adherent agent. The anti-adherent agents include Dimethicone Propyl PG-Betaine, PEG-150/Decyl Alcohol/SMDI Copolymer, Ammonium Acryloyl Dimethyltaurate/Carboxyethyl, Acrylate Crosspolymer, PEG-20 Soy Sterol, PEG/PPG-25/25 Dimethicone, PEG-12 Dimethicone, Dimethicone, Cyclopentasiloxane (and) PEG-12 Dimethicone Crosspolymer, PPG-12-PEG-50 Lanolin, Glycerin (and) Glycine Max (Soybean) Seed Extract, VP/Dimethiconylacrylate/Polycarbamyl/Polyglycol Ester, PEG-10 Sunflower Glycerides, PEG-8 Amodimethicone, PEG/PPG 20/23 Dimethicone Isobutylene/Ethylmaleimide/Hydroxyethylmaleimide Copolymer, Methacryloyl Ethyl Betaine/Acrylates Copolymer, Poloxamer 407, Ethylene Oxide/Propylene Oxide Block Copolymer, PEG-200 Hydrogenated Castor Oil/IPDI Copolymer, PEG-15 Soyamine/IPDI Copolymer Dimer Dilinoleate, Dimethicone PEG-7 Isostearate, PEG-12 Dimethicone, PEG-17 Dimethicone, Polyoxyethylene Polyoxypropylene block copolymer, Polyalkyleneoxide modified silicone copolymer, Disteareth-75 IPDI, and combinations thereof. Various delivery vehicles, including wipes, may be used to deliver the composition to surfaces.

12 Claims, No Drawings

(51) Int. Cl.

| | | |
|---|---|---|
| *A01N 25/08* | (2006.01) | |
| *A01N 37/44* | (2006.01) | |
| *A01N 41/08* | (2006.01) | |
| *A01N 43/36* | (2006.01) | |
| *A01N 45/00* | (2006.01) | |
| *A01N 47/20* | (2006.01) | |
| *A01N 55/00* | (2006.01) | |
| *A01N 63/02* | (2006.01) | |
| *A01N 65/00* | (2009.01) | |
| *C08L 71/02* | (2006.01) | |
| *A61K 8/02* | (2006.01) | |
| *A61Q 17/00* | (2006.01) | |
| *A61K 8/81* | (2006.01) | |
| *A61K 8/86* | (2006.01) | |
| *A61K 8/891* | (2006.01) | |
| *A61K 8/893* | (2006.01) | |
| *A61K 8/895* | (2006.01) | |
| *A61K 8/898* | (2006.01) | |
| *A61K 8/90* | (2006.01) | |
| *A61K 8/92* | (2006.01) | |
| *A61K 8/97* | (2017.01) | |
| *A01N 65/12* | (2009.01) | |
| *A01N 65/18* | (2009.01) | |

(52) U.S. Cl.
CPC .............. *A61K 8/8158* (2013.01); *A61K 8/86* (2013.01); *A61K 8/891* (2013.01); *A61K 8/893* (2013.01); *A61K 8/895* (2013.01); *A61K 8/898* (2013.01); *A61K 8/90* (2013.01); *A61K 8/922* (2013.01); *A61K 8/925* (2013.01); *A61K 8/97* (2013.01); *A61Q 17/005* (2013.01); *C08L 71/02* (2013.01); *A01N 65/12* (2013.01); *A01N 65/18* (2013.01); *C08G 2650/58* (2013.01); *C08L 2203/02* (2013.01); *C08L 2205/02* (2013.01)

(56) References Cited

U.S. PATENT DOCUMENTS

| | | |
|---|---|---|
| 3,494,821 A | 2/1970 | Evans |
| 3,502,538 A | 3/1970 | Petersen |
| 3,502,763 A | 3/1970 | Hartmann |
| 3,542,615 A | 11/1970 | Dobo et al. |
| 3,692,618 A | 9/1972 | Dorschner et al. |
| 3,802,817 A | 4/1974 | Matsuki et al. |
| 3,849,241 A | 11/1974 | Butin et al. |
| 4,007,113 A | 2/1977 | Ostreicher |
| 4,100,324 A | 7/1978 | Anderson et al. |
| 4,144,370 A | 3/1979 | Boulton |
| 4,340,563 A | 7/1982 | Appel et al. |
| 4,361,486 A | 11/1982 | Hou et al. |
| 4,624,890 A | 11/1986 | Lloyd et al. |
| 4,795,668 A | 1/1989 | Krueger et al. |
| 5,057,361 A | 10/1991 | Sayovitz et al. |
| 5,057,368 A | 10/1991 | Largman et al. |
| 5,069,970 A | 12/1991 | Largman et al. |
| 5,108,820 A | 4/1992 | Kaneko et al. |
| 5,162,074 A | 11/1992 | Hills |
| 5,277,976 A | 1/1994 | Hogle et al. |
| 5,284,703 A | 2/1994 | Everhart et al. |
| 5,336,552 A | 8/1994 | Strack et al. |
| 5,350,624 A | 9/1994 | Georger et al. |
| 5,382,400 A | 1/1995 | Pike et al. |
| 5,466,410 A | 11/1995 | Hills |
| 5,512,186 A | 4/1996 | Wright et al. |
| 5,593,599 A | 1/1997 | Wright et al. |
| 5,736,058 A | 4/1998 | Wright et al. |
| 5,742,943 A | 4/1998 | Chen |
| 5,785,179 A | 7/1998 | Buczwinski et al. |
| 5,855,788 A | 1/1999 | Everhart et al. |
| 5,935,883 A | 8/1999 | Pike |
| 5,942,219 A | 8/1999 | Hendriks |
| 5,951,965 A * | 9/1999 | Ansari .............. A61K 49/0006 424/1.11 |
| 5,964,351 A | 10/1999 | Zander |
| 5,989,004 A | 11/1999 | Cook |
| 6,030,331 A | 2/2000 | Zander |
| 6,110,381 A | 8/2000 | Wright |
| 6,123,996 A | 9/2000 | Larsson et al. |
| 6,158,614 A | 12/2000 | Haines et al. |
| 6,180,584 B1 | 1/2001 | Sawan et al. |
| 6,200,669 B1 | 3/2001 | Marmon et al. |
| 6,231,719 B1 | 5/2001 | Garvey et al. |
| 6,241,898 B1 | 6/2001 | Wright et al. |
| 6,248,880 B1 | 6/2001 | Karlson |
| 6,267,996 B1 | 7/2001 | Bombardelli et al. |
| 6,269,969 B1 | 8/2001 | Huang et al. |
| 6,269,970 B1 | 8/2001 | Huang et al. |
| 6,273,359 B1 | 8/2001 | Newman et al. |
| 6,274,041 B1 | 8/2001 | Williamson et al. |
| 6,294,186 B1 | 9/2001 | Beerse et al. |
| 6,306,514 B1 | 10/2001 | Weikel et al. |
| 6,315,864 B2 | 11/2001 | Anderson et al. |
| 6,340,663 B1 | 1/2002 | Deleo et al. |
| 6,515,095 B1 | 2/2003 | Omura et al. |
| 6,565,749 B1 | 5/2003 | Hou et al. |
| 6,630,016 B2 | 10/2003 | Koslow |
| 6,639,066 B2 | 10/2003 | Bostroem et al. |
| 6,696,070 B2 | 2/2004 | Dunn |
| 6,770,204 B1 | 8/2004 | Koslow |
| 6,838,005 B2 | 1/2005 | Tepper et al. |
| 6,916,480 B2 | 7/2005 | Anderson et al. |
| 6,946,196 B2 | 9/2005 | Foss |
| 7,169,304 B2 | 1/2007 | Hughes et al. |
| 7,192,601 B2 | 3/2007 | Walker |
| 7,287,650 B2 | 10/2007 | Koslow |
| 7,288,513 B2 | 10/2007 | Taylor et al. |
| 7,384,762 B2 | 6/2008 | Drocourt et al. |
| 7,432,234 B2 | 10/2008 | Ochomogo et al. |
| 7,569,530 B1 | 8/2009 | Pan et al. |
| 7,576,256 B2 | 8/2009 | Bjoernberg et al. |
| 7,625,844 B1 | 12/2009 | Yang et al. |
| 7,642,395 B2 | 1/2010 | Schroeder et al. |
| 7,795,199 B2 | 9/2010 | Molinaro et al. |
| 7,872,051 B2 | 1/2011 | Clarke |
| 7,985,209 B2 | 7/2011 | Villanueva et al. |
| 7,993,675 B2 | 8/2011 | Oliver et al. |
| 8,034,844 B2 | 10/2011 | Fox et al. |
| 8,293,699 B2 | 10/2012 | Futterer et al. |
| 8,318,654 B2 | 11/2012 | Hoffman et al. |
| 8,343,523 B2 | 1/2013 | Toreki et al. |
| 8,481,480 B1 | 7/2013 | Lam et al. |
| 8,506,978 B2 | 8/2013 | Soerens et al. |
| 8,530,524 B2 | 9/2013 | Wegner et al. |
| 8,603,771 B2 | 12/2013 | Stanley et al. |
| 8,685,178 B2 | 4/2014 | Do et al. |
| 8,771,661 B2 | 7/2014 | MacDonald |
| 8,871,722 B2 | 10/2014 | Harding |
| 9,006,163 B2 | 4/2015 | Hourigan et al. |
| 2001/0040136 A1 | 11/2001 | Wei et al. |
| 2001/0046525 A1 | 11/2001 | Bombardelli et al. |
| 2002/0050016 A1 | 5/2002 | Willman et al. |
| 2002/0189998 A1 | 12/2002 | Haase et al. |
| 2003/0008791 A1 | 1/2003 | Chiang |
| 2003/0069317 A1 | 4/2003 | Seitz et al. |
| 2003/0091540 A1 | 5/2003 | Ahmad et al. |
| 2004/0009141 A1 | 1/2004 | Koenig et al. |
| 2004/0024374 A1 | 2/2004 | Hjorth et al. |
| 2005/0130870 A1 | 6/2005 | Ochomogo et al. |
| 2005/0137540 A1 | 6/2005 | Villanueva et al. |
| 2005/0182021 A1 | 8/2005 | Nichols et al. |
| 2005/0242041 A1 | 11/2005 | Cumberland |
| 2005/0244480 A1* | 11/2005 | Koenig .............. A61K 8/0208 424/443 |
| 2005/0271595 A1 | 12/2005 | Brown |
| 2006/0134239 A1 | 6/2006 | Weide et al. |
| 2006/0140899 A1* | 6/2006 | Koenig .............. A61K 8/4946 424/70.27 |

(56) References Cited

U.S. PATENT DOCUMENTS

| | | |
|---|---|---|
| 2006/0140924 A1* | 6/2006 | Schroeder ............ A61F 13/551 424/94.1 |
| 2006/0193789 A1 | 8/2006 | Tamarkin et al. |
| 2006/0204466 A1 | 9/2006 | Littau et al. |
| 2006/0205619 A1 | 9/2006 | Mayhall et al. |
| 2006/0292086 A1 | 12/2006 | Curtis |
| 2007/0020649 A1 | 1/2007 | Tseng et al. |
| 2007/0141934 A1 | 6/2007 | Sayre et al. |
| 2007/0207104 A1 | 9/2007 | Borish |
| 2007/0237800 A1 | 10/2007 | Lahann |
| 2007/0253926 A1 | 11/2007 | Tadrowski et al. |
| 2007/0286894 A1 | 12/2007 | Marsh et al. |
| 2008/0102053 A1 | 5/2008 | Childers |
| 2008/0275113 A1 | 11/2008 | Huetter et al. |
| 2008/0293613 A1 | 11/2008 | Johnson et al. |
| 2008/0293826 A1* | 11/2008 | Rose ............ A61K 8/31 514/762 |
| 2008/0312118 A1 | 12/2008 | Futterer et al. |
| 2009/0004122 A1 | 1/2009 | Modak et al. |
| 2009/0082472 A1 | 3/2009 | Peters |
| 2009/0087465 A1* | 4/2009 | Doney ............ A61F 13/12 424/402 |
| 2009/0155325 A1 | 6/2009 | Magin et al. |
| 2009/0155327 A1 | 6/2009 | Martin et al. |
| 2009/0191248 A1 | 7/2009 | Hoffman et al. |
| 2009/0226498 A1 | 9/2009 | Flugge-Berendes et al. |
| 2010/0135916 A1* | 6/2010 | Courel ............ A61K 8/046 424/47 |
| 2010/0297029 A1 | 11/2010 | Biering et al. |
| 2011/0009309 A1 | 1/2011 | Mertens et al. |
| 2011/0081528 A1 | 4/2011 | Shannon et al. |
| 2011/0293681 A1 | 12/2011 | Berlin et al. |
| 2012/0046362 A1 | 2/2012 | Kawahara et al. |
| 2012/0121459 A1 | 5/2012 | Edgington et al. |
| 2012/0294911 A1 | 11/2012 | Redmond et al. |
| 2013/0037048 A1 | 2/2013 | Edgington et al. |
| 2013/0209576 A1 | 8/2013 | Brumeister et al. |
| 2013/0274110 A1 | 10/2013 | Westbye et al. |
| 2013/0287724 A1* | 10/2013 | Hoffman ............ A61Q 17/00 424/78.05 |
| 2014/0014584 A1 | 1/2014 | Cone et al. |
| 2014/0147402 A1 | 5/2014 | Klug et al. |
| 2014/0205546 A1 | 7/2014 | Macoviak |
| 2014/0275255 A1 | 9/2014 | Pedersen et al. |
| 2015/0010490 A1* | 1/2015 | Kim ............ A61L 31/16 424/78.17 |
| 2015/0059795 A1 | 3/2015 | Vatter et al. |
| 2015/0290102 A1 | 10/2015 | Cozean et al. |

FOREIGN PATENT DOCUMENTS

| | | | |
|---|---|---|---|
| CN | 103830226 A | 6/2014 | |
| CN | 103845244 A | 6/2014 | |
| CN | 103865692 A | 6/2014 | |
| CN | 104013682 A | 9/2014 | |
| EP | 1046390 A1 | 10/2000 | |
| JP | 63-007785 A | 1/1988 | |
| JP | 10-218940 A | 8/1998 | |
| JP | 2000-110099 A | 4/2000 | |
| JP | 2001-087782 A | 4/2001 | |
| WO | WO 1994/000016 A1 | 1/1994 | |
| WO | WO 2001/028340 A2 | 4/2001 | |
| WO | WO 2001/032132 A2 | 5/2001 | |
| WO | WO 2003/066192 A1 | 8/2003 | |
| WO | WO 2003/092382 A1 | 11/2003 | |
| WO | WO 2004/062703 A1 | 7/2004 | |
| WO | WO 2006/085975 A2 | 8/2006 | |
| WO | WO 2009/065023 A1 | 5/2009 | |
| WO | WO 2010/056685 A2 | 5/2010 | |
| WO | WO 2011/083401 A2 | 7/2011 | |
| WO | WO 2013/016029 A1 | 1/2013 | |
| WO | WO 2013/052545 A1 | 4/2013 | |
| WO | WO 2013/066403 A1 | 5/2013 | |
| WO | WO-2013129719 A1 * | 9/2013 | ............ A61L 31/16 |
| WO | WO 2014/032696 A1 | 3/2014 | |
| WO | WO 2014/113269 A1 | 7/2014 | |
| WO | WO 2014/139904 A1 | 9/2014 | |
| WO | WO 2015/166075 A1 | 11/2015 | |
| WO | WO 2016/018473 A2 | 2/2016 | |
| WO | WO 2016/018474 A1 | 2/2016 | |
| WO | WO 2016/018475 A1 | 2/2016 | |
| WO | WO 2016/018476 A1 | 2/2016 | |

* cited by examiner

ANTI-ADHERENT COMPOSITION

TECHNICAL FIELD

Disclosed is a composition with anti-adherent properties to certain substances. More specifically, disclosed is a composition that includes an anti-adherent agent that does not adhere to certain infectious agents, such as Gram-positive bacteria. The composition may be applied to or incorporated into articles such as wipes, or into ointments, lotions, creams, salves, aerosols, gels, suspensions, sprays, foams, washes, or the like.

BACKGROUND OF THE DISCLOSURE

Communicable human infections pass from person to person through various means such as food, surfaces and hands. For example, in the United States, foodborne pathogens alone cause an estimated 76 million cases of illness, 325,000 hospitalizations and 5,000 deaths per year. This results in the spending or loss of several billion dollars due to absenteeism, cost of medication, and hospitalization.

Foodborne pathogens are typically a result of poor cleaning of hands and surfaces on which food is prepared. In fact, the kitchen is one of the most contaminated sites in the home. For instance, *Staphylococcus aureus* ("*S. aureus*") concentrations can be found in sponges, dishcloths, and the kitchen sink. Of course, these and other Gram-positive microbes lurking elsewhere in the home, at the office, and in public places such as public bathrooms, restaurants, malls, theaters, health-care facilities, etc. Such pathogens can lead to health problems such as bacterial infections.

There are products used today that are used to clean skin and hard surfaces, such as soaps, hand sanitizers, sprays and wipes. However, even the most diligent efforts to keep clean can be hindered by factors such as surface topography, the presence of hair, and the like. These factors can cause pathogens to better adhere to a surface. Other limiting factors include skin sensitivity due to the handling of cleaning products or the application thereof.

There remains a need for compositions that can be applied to surfaces or incorporated into articles, wherein the compositions prevent the adherence of Gram-positive pathogens. Desirably, the compositions are skin friendly, cost effective, and convenient to use.

SUMMARY OF THE DISCLOSURE

In one aspect of the disclosure there is a composition for inhibiting the attachment of microbes to a surface. The composition includes a carrier; and an effective amount of an anti-adherent agent. The agent may be selected from Dimethicone Propyl PG-Betaine, PEG-150/Decyl Alcohol/SMDI Copolymer, Ammonium Acryloyl Dimethyltaurate/Carboxyethyl Acrylate Crosspolymer, PEG-20 Soy Sterol, PEG/PPG-25/25 Dimethicone, PEG-12 Dimethicone, Dimethicone, Cyclopentasiloxane (and) PEG-12 Dimethicone Crosspolymer, PPG-12-PEG-50 Lanolin, Glycerin (and) Glycine Max (Soybean) Seed Extract, VP/Dimethiconylacrylate/Polycarbamyl/Polyglycol Ester, PEG-10 Sunflower Glycerides, PEG-8 Amodimethicone, PEG/PPG 20/23 Dimethicone Isobutylene/Ethylmaleimide/Hydroxyethylmaleimide Copolymer, Methacryloyl Ethyl Betaine/Acrylates Copolymer, Poloxamer 407, Ethylene Oxide/Propylene Oxide Block Copolymer, PEG-200 Hydrogenated Castor Oil/IPDI Copolymer, PEG-15 Soyamine/IPD I Copolymer Dimer Dilinoleate, Dimethicone PEG-7 Isostearate, PEG-12 Dimethicone, PEG-17 Dimethicone, Polyoxyethylene Polyoxypropylene block copolymer, Polyalkyleneoxide modified silicone copolymer, Disteareth-75 IPDI, and combinations thereof.

In yet another aspect of the disclosure there is a wipe made with a nonwoven substrate and an anti-adherent composition that includes 0.01% to 20% (by total weight of composition) of an anti-adherent agent and a hydrophilic liquid carrier. The composition reduces the adherence of *S. aureus* on a surface by at least 0.5 Log according to the High Throughput Anti-adherence Test Method or the Viable Count Anti-Adherence Test Method.

Once the compositions of the present disclosure are applied to a surface and dried, the remaining films do not attract or attach to new microbes, leaving surfaces less apt to harbor microbes.

DETAILED DESCRIPTION OF THE DISLOSURE

The present disclosure is directed to anti-adherent compositions containing an anti-adherent agent and a carrier. The composition may be applied to a surface in the form of a liquid, gel, or foam;

or incorporated into a wash. In addition, the composition may be applied to a surface with a vehicle such as a wipe.

The anti-adherent compositions may be used on biotic surfaces such as skin or plants; or abiotic surfaces such as food prep surfaces; hospital and clinic surfaces; household surfaces; automotive, train, ship and aircraft surfaces; and the like; as long as the surface is compatible with the ingredients of the composition.

According to the High Throughput Anti-adherence Test Method or the Viable Count Anti-Adherence Test Method, infra, the anti-adherent composition reduces adherence to Gram-positive bacteria by at least 0.5 Log, or by at least 0.9 Log, or by at least by 1 Log.

Anti-Adherent Agent

The anti-adherent agents suitable for use in the compositions may include but not be limited to acrylates, acrylate derivatives, polysaccharides, cellulosics, cellulosic derivatives, uerethanes, uerethane derivatives, vinyl derivative, and silicone polyethers.

Suitable polysaccharides may include but not be limited to gums and cellulosics. Suitable nonionic cellulose ethers, for instance, may be produced in any manner known to those skilled in the art, such as by reacting alkali cellulose with ethylene oxide and/or propylene oxide, followed by reaction with methyl chloride, ethyl chloride and/or propyl chloride. Nonionic cellulosic ethers and methods for producing such ethers are described, for instance, in U.S. Pat. No. 6,123,996 to Larsson, et al.; U.S. Pat. No. 6,248,880 to Karlson; and U.S. Pat. No. 6,639,066 to Bostrom, et al., which are incorporated herein in their entirety by reference thereto for all purposes. Some suitable examples of nonionic cellulosic ethers include, but are not limited to, water-soluble alkyl cellulose ethers, such as methyl cellulose and ethyl cellulose; hydroxyalkyl cellulose ethers, such as hydroxyethyl cellulose, hydroxypropyl cellulose, hydroxypropyl hydroxybutyl cellulose, hydroxyethyl hydroxypropyl cellulose, hydroxyethyl hydroxybutyl cellulose, and hydroxyethyl hydroxypropyl hydroxybutyl cellulose; alkyl hydroxyalkyl cellulose ethers, such as methyl hydroxyethyl cellulose, ethyl hydroxyethyl cellulose, ethyl hydroxypropyl cellulose, methyl ethyl hydroxyethyl cellulose, and methyl ethyl hydroxypropyl cellulose; and so forth. Particularly suitable nonionic cellulosic ethers for use in the present disclosure are hydroxypropyl methylcellulose, cellulose gum, and methylcellulose.

Gums are also suitable materials for use as the anti-adherent agent. The materials in this group are generally plant-derived materials which belong to the chemical class of carbohydrates. Although chemically diverse, the unique ability of gums to swell in the presence of water and to increase the viscosity of aqueous preparations accounts for this special class. The viscosity developed by hydrophilic colloids depends on their molecular weight and the presence of various cations which may neutralize some acid functions of these carbohydrate molecules or cause some cross linking. In cosmetics, gums and the like are used to impart viscosity to all types of products. They act as suspending or gelling agents and emulsion stabilizers. Some of these gums have unique textural qualities which make them useful in water-based lubricants. Suitable gums for use in the present disclosure may include but not be limited to Acacia Catechu Gum, Acacia Farnesiana Gum, Acacia Senegal Gum, Acacia Seyal Gum, Acacia Seyal Gum Octenylsuccinate, Agar, Algin, Alginic Acid, Ammonium Alginate, Amylopectin, Ascorbyl Methylsilanol Pectinate, Astragalus Gummifer Gum, Boswellia Serrata Gum, Caesalpinia Spinosa Gum, Calcium Alginate, Calcium Carboxymethyl Cellulose, Calcium Carrageenan, Carboxybutyl Chitosan, Carboxymethyl Cellulose Acetate Butyrate, Carboxymethyl Chitin, Carboxymethyl Dextran, Carboxymethyl Hydroxyethylcellulose, Carboxymethyl Hydroxypropyl Guar, Carrageenan, Cassia Gum, Cellulose Gum, Ceratonia Siliqua (Carob) Gum, Cyamopsis Tetragonoloba (Guar) Gum, Dehydroxanthan Gum, Dextran, Dextran Sulfate, Dextrin, Dextrin Behenate, Gelatin, Gelatin Crosspolymer, Gellan Gum, Ghatti Gum, Glyceryl Alginate, Glyceryl Starch, Guar Hydroxypropyltrimonium Chloride, Hydrolyzed Caesalpinia Spinosa Gum, Hydrolyzed Carrageenan, Hydrolyzed Cellulose Gum, Hydrolyzed Ceratonia Siliqua Gum Extract, Galactoarabinan, Hydrolyzed Furcellaran, Hydrolyzed Gelatin, Hydrolyzed Guar, Hydrolyzed Pectin, Hydrolyzed Rhizobian Gum, Hydrolyzed Sclerotium Gum, Hydroxybutyl Methylcellulose, Hydroxyethylcellulose, Hydroxyethyl Ethylcellulose, Hydroxypropylcellulose, Hydroxypropylcellulose, Hydroxypropyl Chitosan, Hydroxypropyl Methylcellulose, Hydroxypropyl Methylcellulose Acetate/Succinate, Hydroxypropyl Methylcellulose Stearoxy Ether, Hydroxypropyl Oxidized Starch, Hydroxypropyl Starch, Hydroxypropyl Xanthan Gum, Locust Bean Hydroxypropyltrimonium Chloride, Magnesium Alginate, Maltodextrin, Methylamido Cellulose Gum, Methylcellulose, Methyl Hydroxyethylcellulose, Methylsilanol Carboxymethyl Theophylline Alginate, Natto Gum, Nonoxynyl Hydroxyethylcellulose, Olibanum, Pectin, Pistacia Lentiscus (Mastic) Gum, Potassium Alginate, Potassium Carrageenan, Potassium, Propylene Glycol Alginate, Prunus Persica (Peach) Gum, Rhizobian Gum, Sclerotium Gum, Sodium Algin Sulfate, Sodium Carboxymethyl Chitin, Sodium Carboxymethyl Dextran, Sodium Carboxymethyl Beta-Glucan, Sodium Carboxymethyl Starch, Sodium Carrageenan, Sodium Cellulose Sulfate, Sodium Polyacrylate Starch, Sodium Stearoxy PG-Hydroxyethylcellulose Sulfonate, Sodium/TEA-Undecylenoyl Alginate, Sodium/TEA-Undecylenoyl Carrageenan, Sterculia Urens Gum, Styrax Benzoin Gum, Tamarindus Indica Seed Gum, TEA-Alginate, Undecylenoyl Xanthan Gum, Welan Gum, Xanthan Gum.

Still another suitable example of anti-adherent agents may include acrylates and acrylate derivatives. Suitable examples include, but are be limited to, Ammonium Acryloyl Dimethyltaurate/Carboxyethyl Acrylate Crosspolymer and Methacryloyl Ethyl Betaine/Acrylates Copolymer and combinations thereof.

Another class of anti-adherent agents includes polyesters, which are manufactured by polymerizing organic acids and alcohols. Of particular interest are polyesters that are water soluble or dispersible.

Another class of anti-adherent agent is Polyimides. One example is Polyimide-1, a terpolymer that is made by reacting poly(isobutylene-alt-maleic anhydride) with dimethylaminopropylamine and methoxy-PEG/PPG-31/9-2-propylamine in a mixture of ethanol and Water (q.v.). The resulting polymer contains both imide, ester, and acid functionality and is used in skin and hair care preparations as a film forming agent. Another example of imide is lsobutylene/Ethylmaleimide/ Hydroxyethylmaleimide Copolymer.

A further class of anti-adherent agents include Polyquaternium compounds. Polyquaterniums have been used in cosmetic industry for a long time and are known for their substantivity to hair and skin.

Another suitable anti-adherent agent may include a modified silicone having a polyether moeity. As used herein, the term "silicone" generally refers to a broad family of synthetic polymers that have a repeating silicon-oxygen backbone, including, but not limited to, polydimethylsiloxane and polysiloxanes having hydrogen-bonding functional groups selected from the group consisting of amino, carboxyl, hydroxyl, ether, polyether, aldehyde, ketone, amide, ester, and thiol groups. A specific example may include but not be limited to Dimethicone.

Additional silicones suitable for use as anti-adherent agents would be silicones containing a polyether moiety. The polyether moiety could be a PG, PEG or PPG or combinations thereof. Suitable examples could be but not be limited to Dimethicone Propyl PG-Betaine, PEG/PPG-25/25 Dimethicone, PEG/PPG 20/23 Dimethicone, PEG-12 Dimethicone, Dimethicone, PEG-8 Amine Dimethicone, PEG-7 Isostearate, PEG-17 Dimethicone, Cyclopentasiloxane (and) PEG-12 Dimethicone Crosspolymer, and Polyalkyleneoxide modified silicone copolymer and combinations thereof.

Another class of anti-adherent agents is copolymers of PEG, PPG or combination thereof. Specifically, Poloxamers that are nonionic triblock copolymers composed of a central hydrophobic chain of polyoxypropylene (poly(propylene oxide)) flanked by two hydrophilic chains of polyoxyethylene (poly(ethylene oxide)) fall under this category. Because the lengths of the polymer blocks can be customized, many different poloxamers exist that have slightly different properties. Suitable agents are Poloxamer 407 (PLURONIC F127 available from BASF, Florham Park, N.J.) and Ethylene oxide/propylene oxide block copolymer (PLURONIC L 105 available from BASF, Florham Park, N.J.).

In one example, PEG, PPG moiety can be attached to a fatty acid, a fatty alcohol, or lanolin. Specific examples include but not limited to PEG-20 Soy Sterol, PPG-12-PEG-50 Lanolin, Glycerin (and) Glycine Max (Soybean) Seed Extract, PEG-10 Sunflower Glycerides and combinations thereof.

Another suitable anti-adherent agent may include a urethane or urethane derivative. Polyurethane is a polymer composed of a chain of organic units joined by carbamate or urethane moieties. Polyisocyanate is typically reacted with various polyols and other functional groups to create a broad range of physcial characteristics and film forming properties. For this disclosure, particularly useful commercially available urethane polymers are rendered hydrophilic inclusion of polyethylene glycol or other highly hydrophilic moieties. Without being bound to any particular theory, the inclusion of hydrophilic moieties, particularly when added in a pendant fashion to the polymer, creates a sphere of hydration in which water molecules are tightly bound to the side chains of the polymer. Unable to remove the water, bacteria are unable to effectively bind to the surface. Also, it may be advantageous to include dimethicone, vinylpyrlidone or acrylate based monomers within the polymer backbone itself to provide substantivity coating to the surface of interest. Particularly useful commercially available polyurethanes for the present disclosure include but are not limited to PEG-150/Decyl Alcohol/SMDI Copolymer, VP/Dimethiconylacrylate/Polycarbamyl/Polyglycol Ester, PEG-200 Hydrogenated Castor Oil/IPDI Copolymer, IPDI/PEG-15 Soyamine Copolymer Dimer Dilinoleate and Disteareth-75 IPDI and combinations thereof.

Referring to Table 1, anti-adherent agents suitable for use in the present disclosure include silicones, synthetic polymers, emulsifiers, emollients, polysaccharides, ethoxylated natural alcohols, and naturally derived emulsifiers. Specifically, these include, but are not limited to the following: Dimethicone Propyl PG-Betaine, PEG-150/Decyl Alcohol/SMDI Copolymer, Ammonium Acryloyl Dimethyltaurate/Carboxyethyl Acrylate Crosspolymer PEG-20 Soy Sterol, PEG/PPG-25/25 Dimethicone, PEG-12 Dimethicone, Cyclopentasiloxane (and) PEG-12 Dimethicone Crosspolymer, PPG-12-PEG-50 Lanolin, Glycerin (and) Glycine Max (Soybean) Seed Extract, VP/Dimethiconylacrylate/Polycarbamyl/Polyglycol Ester, PEG-10 Sunflower Glycerides, PEG-8 Amodimethicone, PEG/PPG 20/23 Dimethicone Isobutylene/Ethylmaleimide/Hydroxyethylmaleimide Copolymer, Methacryloyl Ethyl Betaine/Acrylates Copolymer, Poloxamer 407, Ethylene Oxide/Propylene Oxide Block Copolymer, PEG-200 Hydrogenated Castor Oil/IPDI Copolymer, PEG-15 Soyamine/IPDI Copolymer Dimer Dilinoleate, Dimethicone PEG-7 Isostearate, PEG-12 Dimethicone, PEG-17 Dimethicone, Polyoxyethylene Polyoxypropylene block copolymer, Polyalkyleneoxide modified silicone copolymer, Disteareth-75 IPDI, and combinations thereof. These anti-adherent agents perform adequately and vary in anti-adherency to *S. aureus* as shown in Table 2, infra.

TABLE 1

Anti-Adherent Agents

| Agent | INCI | Description | Manufacturer |
| --- | --- | --- | --- |
| ABIL B 9950 | Dimethicone Propyl PG-Betaine | Silicone | Evonik, Eseen, Germany |
| ACULYN 44 | PEG-150/Decyl Alcohol/SMDI Copolymer | Synthetic Polymer | Dow Chemical |
| ARISTOFLEX TAC | Ammonium Acryloyl Dimethyltaurate/Carboxyethyl and Acrylate Crosspolymer | Synthetic Polymer | Clariant, Muttenz, Switzerland |
| BARNET BPS 20 | PEG-20 Soy Sterol | Emollient | Barnet, Englewood Cliffs, NJ |
| BELSIL DMC 6031 | PEG/PPG-25/25 Dimethicone | Silicone | Wacker, Munich Germany |
| DC 193 | PEG-12 Dimethicone | Silicone | Dow Corning, Midland, MI |
| DC 200 (100 CST) | Dimethicone | Silicone | Dow Corning, Midland, MI |
| DC 9011 | Cyclopentasiloxane (and) PEG-12 Dimethicone Crosspolymer | Silicone | Dow Corning, Midland, MI |
| LANEXOL AWS | PPG-12-PEG-50 Lanolin | Ethoxylated natural alcohols | Croda, Edison, NJ |
| LYSOFIX | Glycerin (and) *Glycine Max* (Soybean) Seed Extract | Naturally derived emulsifier | Kemin, Des Moines, IA |
| PECOGEL S1120 | VP/Dimethiconylacrylate/Polycarbamyl/Polyglycol Ester | Synthetic Polymer | Phoenix Chemicals |
| FLORASOLVS PEG-10 Sunflower | PEG-10 Sunflower Glycerides | Emollient | Floratech, Chandler, AZ |
| SILAMINE C300 | PEG-8 Amodimethicone | Silicone | Siltech, Toronto, Canada |
| SILSOFT 440 | PEG/PPG 20/23 Dimethicone | Silicone | Momentive, Columbus, OH |
| Aquaflex FX-64 | Isobutylene/Ethylmaleimide/Hydroxyethylmaleimide Copolymer | Synthetic Polymer | Ashland, Inc, Wilmington, DE |
| Diaformer Z-301N | Methacryloyl Ethyl Betaine/Acrylates Copolymer | Synthetic Polymer | Clariant International, Charlotte, NC |
| Pluronic F 127 | Poloxamer 407 | Synthetic Polymer | BASFCorporation, Florham Park, NJ |
| Pluronic L 105 | Ethylene Oxide/Propylene Oxide Block Copolymer | Synthetic Polymer | BASFCorporation, Florham Park, NJ |
| Polyderm PPI-CO-200 | PEG-200 Hydrogenated Castor Oil/IPDI Copolymer | Synthetic Polymer | Alzo International, Sayreville, NJ |
| PolyNecon™ PPI-SA-15D | PEG-15 Soyamine/IPDI Copolymer Dimer Dilinoleate | Synthetic Polymer | Alzo International, Sayreville, NJ |
| Silsense DW-18 Silicone | Dimethicone PEG-7 Isostearate | Silicone | Lubrizol Advanced Materials, Cleveland, OH |
| Silsoft 875 | PEG-12 Dimethicone | Silicone | Momentive Performance Materials, Friendly, WV |

TABLE 1-continued

Anti-Adherent Agents

| Agent | INCI | Description | Manufacturer |
|---|---|---|---|
| Silsoft 895 | PEG-17 Dimethicone | Silicone | Momentive Performance Materials, Friendly, WV |
| UCON TPEG-500 | Polyoxyethylene Polyoxypropylene block copolymer | Synthetic polymer | Dow Corning, Midland, MI |
| NuWet 237 | Polyalkyleneoxide modified silicone copolymer | Silicone | Momentive, Terrytown NY |
| Dermothix 75 Liquid | Disteareth-75 IPDI | Synthetic polymer | Alzo International, Sayreville, NJ |

The anti-adherent compositions of the present disclosure can be suitably made with an anti-adherent agent in an amount of from about 0.01% (by the total weight of the composition), to about 20% (by total weight of the composition), or from about 0.05% (by total weight of the composition) to about 15% (by total weight of the composition), or from about 0.1% (by total weight of the composition) to about 10% (by total weight of the composition).

Carriers

The anti-adherent compositions of the present disclosure may be formulated with one or more conventional and compatible carrier materials. The anti-adherent composition may take a variety of forms including, without limitation, aqueous solutions, gels, balms, lotions, suspensions, creams, milks, salves, ointments, sprays, emulsions, oils, resins, foams, solid sticks, aerosols, and the like. Liquid carrier materials suitable for use in the instant disclosure include those well-known for use in the cosmetic and medical arts as a basis for ointments, lotions, creams, salves, aerosols, gels, suspensions, sprays, foams, washes, and the like, and may be used in their established levels.

Non-limiting examples of suitable carrier materials include water, emollients, humectants, polyols, surfactants, esters, silicones, clays, and other pharmaceutically acceptable carrier materials.

In one embodiment, the anti-adherent compositions can optionally include one or more emollients, which typically act to soften, soothe, and otherwise lubricate and/or moisturize the skin. Suitable emollients that can be incorporated into the compositions include oils such as alkyl dimethicones, alkyl methicones, alkyldimethicone copolyols, phenyl silicones, alkyl trimethylsilanes, dimethicone, dimethicone crosspolymers, cyclomethicone, lanolin and its derivatives, fatty esters, glycerol esters and derivatives, propylene glycol esters and derivatives, alkoxylated carboxylic acids, alkoxylated alcohols, fatty alcohols, and combinations thereof.

The anti-adherent compositions may include one or more emollients in an amount of from about 0.01% (by total weight of the composition) to about 20% (by total weight of the composition), or from about 0.05% (by total weight of the composition) to about 10% (by total weight of the composition), or from about 0.10% (by total weight of the composition) to about 5% (by total weight of the composition).

In another embodiment the anti-adherent compositions include one or more esters. The esters may be selected from cetyl palmitate, stearyl palmitate, cetyl stearate, isopropyl laurate, isopropyl myristate, isopropyl palmitate, and combinations thereof. The fatty alcohols include octyldodecanol, lauryl, myristyl, cetyl, stearyl, behenyl alcohol, and combinations thereof. Ethers such as eucalyptol, ceteraryl glucoside, dimethyl isosorbic polyglyceryl-3 cetyl ether, polyglyceryl-3 decyltetradecanol, propylene glycol myristyl ether, and combinations thereof can also suitably be used as emollients. Other suitable ester compounds for use in the anti-adherent compositions or the present disclosure are listed in the *International Cosmetic Ingredient Dictionary and Handbook,* 11th Edition, CTFA, (January, 2006) ISBN-10:1882621360, ISBN-13: 978-1882621361, and in the 2007 *Cosmetic Bench Reference*, Allured Pub. Corporation (Jul. 15, 2007) ISBN-10: 1932633278, ISBN-13: 978-1932633276, both of which are incorporated by reference herein to the extent they are consistent herewith.

Humectants that are suitable as carriers in the anti-adherent compositions of the present disclosure include, for example, glycerin, glycerin derivatives, hyaluronic acid, hyaluronic acid derivatives, betaine, betaine derivatives amino acids, amino acid derivatives, glycosaminoglycans, glycols, polyols, sugars, sugar alcohols, hydrogenated starch hydrolysates, hydroxy acids, hydroxy acid derivatives, salts of PCA and the like, and combinations thereof. Specific examples of suitable humectants include honey, sorbitol, hyaluronic acid, sodium hyaluronate, betaine, lactic acid, citric acid, sodium citrate, glycolic acid, sodium glycolate ,sodium lactate, urea, propylene glycol, butylene glycol, pentylene glycol, ethoxydiglycol, methyl gluceth-10, methyl gluceth-20, polyethylene glycols (as listed in the *International Cosmetic Ingredient Dictionary and Handbook* such as PEG-2 through PEG 10), propanediol, xylitol, maltitol, or combinations thereof. Humectants are beneficial in that they prevent or reduce the chance that the anti-adherent film, formed after the anti-adherent agent is applied to a surface, will crack.

The anti-adherent compositions of the disclosure may include one or more humectants in an amount of about 0.01% (by total weight of the composition) to about 20% (by total weight of the composition), or about 0.05% (by total weight of the composition) to about 10% by total weight of the composition), or about 0.1% (by total weight of the composition) to about 5.0% (by total weight of the composition).

The anti-adherent compositions may include water. For instance, where the anti-adherent composition is a wetting composition, such as described below for use with a wet wipe, the composition will typically include water. The anti-adherent compositions can suitably comprise water in an amount of from about 0.01% (by total weight of the composition) to about 99.98% (by total weight of the composition), or from about 0.05% (by total weight of the composition) to about 95% (by total weight of the composition), or from about 0.10% (by total weight of the composition) to about 90% (by total weight of the composition).

In an embodiment where the anti-adherent composition serves as a wash (e.g. shampoo; surface cleanser; or hand, face, or body wash), the anti-adherent composition will include one or more surfactants. These may be selected from anionic, cationic, nonionic and amphoteric surfactants. Amounts may range from 0.1 to 30%, or from 1 to 20%, or from 3 to 15% by total weight of the total composition.

Suitable anionic surfactants include, but are not limited to, $C_8$ to $C_{22}$ alkane sulfates, ether sulfates and sulfonates. Among the suitable sulfonates are primary $C_8$ to $C_{22}$ alkane sulfonate, primary $C_8$ to $C_{22}$ alkane disulfonate, $C_8$ to $C_{22}$ alkene sulfonate, $C_8$ to $C_{22}$ hydroxyalkane sulfonate or alkyl glyceryl ether sulfonate. Specific examples of anionic surfactants include ammonium lauryl sulfate, ammonium laureth sulfate, triethylamine lauryl sulfate, triethylamine laureth sulfate, triethanolamine lauryl sulfate, triethanolamine laureth sulfate, monoethanolamine lauryl sulfate, monoethanolamine laureth sulfate, diethanolamine lauryl sulfate, diethanolamine laureth sulfate, lauric monoglyceride sodium sulfate, sodium lauryl sulfate, sodium laureth sulfate, potassium laureth sulfate, sodium lauryl sarcosinate, sodium lauroyl sarcosinate, potassium lauryl sulfate, sodium trideceth sulfate, sodium methyl lauroyl taurate, sodium lauroyl isethionate, sodium laureth sulfosuccinate, sodium lauroyl sulfosuccinate, sodium tridecyl benzene sulfonate, sodium dodecyl benzene sulfonate, sodium lauryl amphoacetate and mixtures thereof. Other anionic surfactants include the $C_8$ to $C_{22}$ acyl glycinate salts. Suitable glycinate salts include sodium cocoylglycinate, potassium cocoylglycinate, sodium lauroylglycinate, potassium lauroylglycinate, sodium myristoylglycinate, potassium myristoylglycinate, sodium palmitoylglycinate, potassium palmitoylglycinate, sodium stearoylglycinate, potassium stearoylglycinate, ammonium cocoylglycinate and mixtures thereof. Cationic counterions to form the salt of the glycinate may be selected from sodium, potassium, ammonium, alkanolammonium and mixtures of these cations.

Suitable cationic surfactants include, but are not limited to alkyl dimethylamines, alkyl amidopropylamines, alkyl imidazoline derivatives, quaternised amine ethoxylates, and quaternary ammonium compounds.

Suitable nonionic surfactants include, but are not limited to, alcohols, acids, amides or alkyl phenols reacted with alkylene oxides, especially ethylene oxide either alone or with propylene oxide. Specific nonionics are $C_6$ to $C_{22}$ alkyl phenols-ethylene oxide condensates, the condensation products of $C_8$ to $C_{13}$ aliphatic primary or secondary linear or branched alcohols with ethylene oxide, and products made by condensation of ethylene oxide with the reaction products of propylene oxide and ethylenediamine. Other nonionics include long chain tertiary amine oxides, long chain tertiary phosphine oxides and dialkyl sulphoxides, alkyl polysaccharides, amine oxides, block copolymers, castor oil ethoxylates, ceto-oleyl alcohol ethoxylates, ceto-stearyl alcohol ethoxylates, decyl alcohol ethoxylates, dinonyl phenol ethoxylates, dodecyl phenol ethoxylates, end-capped ethoxylates, ether amine derivatives, ethoxylated alkanolamides, ethylene glycol esters, fatty acid alkanolamides, fatty alcohol alkoxylates, lauryl alcohol ethoxylates, monobranched alcohol ethoxylates, natural alcohol ethoxylates, nonyl phenol ethoxylates, octyl phenol ethoxylates, oleyl amine ethoxylates, random copolymer alkoxylates, sorbitan ester ethoxylates, stearic acid ethoxylates, stearyl amine ethoxylates, synthetic alcohol ethoxylates, tall oil fatty acid ethoxylates, tallow amine ethoxylates and trid tridecanol ethoxylates.

Suitable zwitterionic surfactants include, for example, alkyl amine oxides, silicone amine oxides, and combinations thereof. Specific examples of suitable zwitterionic surfactants include, for example, 4-[N,N-di(2-hydroxyethyl)-N-octadecylammonio]-butane-1-carboxylate, S-[S-3-hydroxypropyl-S-hexadecylsulfonio]-3-hydroxypentane-1-sulfate, 3-[P,P-diethyl-P-3,6,9-trioxatetradexopcylphosphonio]-2-hydroxypropane-1-phosphate, 3-[N,N-dipropyl-N-3-dodecoxy-2-hydroxypropylammonio]-propane-1-phosphonate, 3-(N,N-dimethyl-N-hexadecylammonio)propane-1-sulfonate, 3-(N,N-dimethyl-N-hexadecylammonio)-2-hydroxypropane-1-sulfonate, 4-[N,N-di(2-hydroxyethyl)-N-(2-hydroxydodecyl)ammonio]-butane-1-carboxylate, 3-[S-ethyl-S-(3-dodecoxy-2-hydroxypropyl)sulfonio]-propane-1-phosphate, 3-[P,P-d imethyl-P-dodecylphosphonio]-propane-1-phosphonate, 5-[N,N-di(3-hydroxypropyl)-N-hexadecylammonio]-2-hydroxy-pentane-1-sulfate, and combinations thereof.

Suitable amphoteric surfactants include, but are not limited to, derivatives of aliphatic quaternary ammonium, phosphonium, and sulfonium compounds, in which the aliphatic radicals can be straight or branched chain, and wherein one of the aliphatic substituents contains from about 8 to about 18 carbon atoms and one substituent contains an anionic group, e.g., carboxy, sulfonate, sulfate, phosphate, or phosphonate. Illustrative amnphoterics are coco dimethyl carboxymethyl betaine, cocoamidopropyl betaine, cocobetaine, oleyl betaine, cetyl dimethyl carboxymethyl betaine, lauryl bis-(2-hydroxyethyl) carboxymethyl betaine, stearyl bis-(2-hydroxypropyl) carboxymethyl betaine, oleyl dimethyl gamma-carboxypropyl betaine, lauryl bis-(2-hydroxypropyl)alpha-carboxyethyl betaine, cocoamphoacetates, and combinations thereof. The sulfobetaines may include stearyl dimethyl sulfopropyl betaine, lauryl dimethyl sulfoethyl betaine, lauryl bis-(2-hydroxyethyl) sulfopropyl betaine and combinations thereof.

Rheology Modifier

Optionally, one or more rheology modifiers, such as thickeners, may be added to the anti-adherent compositions. Suitable rheology modifiers are compatible with the anti-adherent agent. As used herein, "compatible" refers to a compound that, when mixed with the anti-adherent agent, does not adversely affect the anti-adherent properties of same.

A thickening system is used in the anti-adherent compositions to adjust the viscosity and stability of the compositions. Specifically, thickening systems prevent the composition from running off of the hands or body during dispensing and use of the composition. When the anti-adherent composition is used with a wipe product, a thicker formulation can be used to prevent the composition from migrating from the wipe substrate.

The thickening system should be compatible with the compounds used in the present disclosure; that is, the thickening system, when used in combination with the anti-adherent compounds, should not precipitate out, form a coacervate, or prevent a user from perceiving the conditioning benefit (or other desired benefit) to be gained from the composition. The thickening system may include a thickener which can provide both the thickening effect desired from the thickening system and a conditioning effect to the user's skin.

Thickeners may include, cellulosics, gums, acrylates, starches and various polymers. Suitable examples include are not limited to hydroxethyl cellulose, xanthan gum, guar gum, potato starch, and corn starch. In some embodiments, PEG-150 stearate, PEG-150 distearate, PEG-175 diisostearate, polyglyceryl-10 behenate/eicosadioate, distareth-100 IPDI, polyacrylamidomethylpropane sulfonic acid, butylated PVP, and combinations thereof may be suitable.

While the viscosity of the compositions will typically depend on the thickener used and the other components of the compositions, the thickeners of the compositions suitably provide for compositions having a viscosity in the range of greater than 10 cP to about 30,000 cP or more. In another embodiment, the thickeners provide compositions having a viscosity of from about 100 cP to about 20,000 cP. In yet another embodimentthickeners provide compositions having a viscosity of from about 200 cP to about 15,000 cP.

Typically, the anti-adherent compositions of the present disclosure include the thickening system in an amount of no more than about 20% (by total weight of the composition), or from about 0.01% (by total weight of the composition) to about 20% (by total weight of the composition). In another aspect the thickening system is present in the anti-adherent composition in an amount of from about 0.05% (by total weight of the composition) to about 15% (by total weight of the composition), or from about 0.075% (by total weight of the composition) to about 10% (by total weight of the composition), or from about 0.1% (by total weight of the composition) to about 7.5% (by total weight of the composition).

Foaming Agents

In one embodiment, the anti-adherent compositions are delivered as a foam. In accordance with the present disclosure, in order to make the composition foamable, the alcohol is combined with a foaming agent such as at least one derivatized dimethicone.

The foaming agent is capable of causing the compositions to foam when the compositions are combined with air using, for instance, a manual pump dispenser. Although the anti-adherent compositions may be dispensed from an aerosol container, an aerosol is not needed in order to cause the compositions to foam. Also of particular advantage, the compositions are foamable without having to include fluorinated surfactants.

Various different derivatized dimethicone foaming agents may be used in the compositions of the present disclosure. The derivatized dimethicone, for instance, may comprise a dimethicone copolyol, such as an ethoxylated dimethicone. In one embodiment, the derivatized dimethicone is linear, although branched dimethicones may be used.

The amount of foaming agent present in the foaming compositions can depend upon various factors and the desired result. In general, the foaming agent can be present in an amount from about 0.01% to about 10% by weight, or from about 0.1% to about 5% by weight, or from about 0.1% to about 2% by weight.

When an anti-adherent composition is made foamable, it may be contained in an aerosol container. In an aerosol container, the composition is maintained under pressure sufficient to cause foam formation when dispensed.

Emulsifiers

In one embodiment, the anti-adherent compositions may include hydrophobic and hydrophilic ingredients, such as a lotion or cream. Generally, these emulsions have a dispersed phase and a continuous phase, and are generally formed with the addition of a surfactant or a combination of surfactants with varying hydrophilic/lipopiliclipophilic balances (HLB). Suitable emulsifiers include surfactants having HLB values from 0 to 20, or from 2 to 18. Suitable non-limiting examples include Ceteareth-20, Cetearyl Glucoside, Ceteth-10, Ceteth-2, Ceteth-20, Cocamide MEA, Glyceryl Laurate, Glyceryl Stearate, PEG-100 Stearate, Glyceryl Stearate, Glyceryl Stearate SE, Glycol Distearate, Glycol Stearate, Isosteareth-20, Laureth-23, Laureth-4, Lecithin, Methyl Glucose Sesquistearate, Oleth-10, Oleth-2, Oleth-20, PEG-100 Stearate, PEG-20 Almond Glycerides, PEG-20 Methyl Glucose Sesquistearate, PEG-25 Hydrogenated Castor Oil, PEG-30 Dipolyhydroxystearate, PEG-4 Dilaurate, PEG-40 Sorbitan Peroleate, PEG-60 Almond Glycerides, PEG-7 Olivate, PEG-7 Glyceryl Cocoate, PEG-8 Dioleate, PEG-8 Laurate, PEG-8 Oleate, PEG-80 Sorbitan Laurate, Polysorbate 20, Polysorbate 60, Polysorbate 80, Polysorbate 85, Propylene Glycol Isostearate, Sorbitan Isostearate, Sorbitan Laurate, Sorbitan Monostearate, Sorbitan Oleate, Sorbitan Sesquioleate, Sorbitan Stearate, Sorbitan Trioleate, Stearamide MEA, Steareth-100, Steareth-2, Steareth-20, Steareth-21. The compositions can further include surfactants or combinations of surfactants that create liquid crystalline networks or liposomal networks. Suitable non-limiting examples include OLIVEM 1000 (INCI: Cetearyl Olivate (and) Sorbitan Olivate (available from HallStar Company (Chicago, Ill.)); ARLACEL LC (INCI: Sorbitan Stearate (and) Sorbityl Laurate, commercially available from Croda (Edison, N.J.)); CRYSTALCAST MM (INCI: Beta Sitosterol (and) Sucrose Stearate (and) Sucrose Distearate (and) Cetyl Alcohol (and) Stearyl Alcohol, commercially available from MMP Inc. (South Plainfield, N.J.)); UNIOX CRISTAL (INCI: Cetearyl Alcohol (and) Polysorbate 60 (and) Cetearyl Glucoside, commercially available from Chemyunion (Sao Paulo, Brazil)). Other suitable emulsifiers include lecithin, hydrogenated lecithin, lysolecithin, phosphatidylcholine, phospholipids, and combinations thereof.

Adjunct Ingredients

The anti-adherent compositions of the present disclosure may additionally include adjunct ingredients conventionally found in pharmaceutical compositions in an established fashion and at established levels. For example, the anti-adherent compositions may comprise additional compatible pharmaceutically active and compatible materials for combination therapy, such as antioxidants, anti-parasitic agents, antipruritics, antifungals, antiseptic actives, biological actives, astringents, keratolytic actives, local anaesthetics, anti-stinging agents, anti-reddening agents, skin soothing agents, external analgesics, film formers, skin exfoliating agents, sunscreens, and combinations thereof.

Other suitable additives that may be included in the anti-adherent compositions of the present disclosure include compatible colorants, deodorants, emulsifiers, anti-foaming agents (when foam is not desired), lubricants, skin conditioning agents, skin protectants and skin benefit agents (e.g., aloe vera and tocopheryl acetate), solvents, solubilizing agents, suspending agents, wetting agents, pH adjusting ingredients (a suitable pH range of the compositions can be from about 3.5 to about 8), chelators, propellants, dyes and/or pigments, and combinations thereof.

Another component that may be suitable for addition to the anti-adherent compositions is a fragrance. Any compatible fragrance may be used. Typically, the fragrance is present in an amount from about 0% (by weight of the composition) to about 5% (by weight of the composition), and more typically from about 0.01% (by weight of the composition) to about 3% (by weight of the composition). In one desirable embodiment, the fragrance will have a clean, fresh and/or neutral scent to create an appealing delivery vehicle for the end consumer.

Organic sunscreens that may be present in the anti-adherent compositions include ethylhexyl methoxycinnamate, avobenzone, octocrylene, benzophenone-4, phenylbenzimidazole sulfonic acid, homosalate, oxybenzone, benzophenone-3, ethylhexyl salicylate, and mixtures thereof.

Antimicrobial agents may be added to the anti-adherent compositions. For example, suitable antimicrobials include biocides such as a short-chain alcohol, benzoalkonium chloride ("BAC"), didecyl dimethyl ammonium chloride ("DDAC"), and zeolite ("CWT-A"). Other possible antimicrobial agents include: isothiazolone, alkyl dimethyl ammonium chloride, a triazine, 2-thiocyanomethylthio benzothiazol, methylene bis thiocyanate, acrolein, dodecylguanidine hydrochloride, a chlorophenol, a quaternary ammonium salt, gluteraldehyde, a dithiocarbamate, 2-mercatobenzothiazole, para-chloro-meta-xylenol, silver, chlorohexidine, polyhexamthylene biguanide, a n-halamine, triclosan, a phospholipid, an alpha hydroxyl acid, 2,2-dibromo-3-nitrilopropionamide, 2-bromo-2-nitro-1,3-propanediol, farnesol, iodine, bromine, hydrogen peroxide, chlorine dioxide, a botanical oil, a botanical extract, benzalkonium chloride, chlorine, sodium hypochlorite, or combinations thereof.

When present, the amount of the antimicrobial agent in the anti-adherent compositions is in an amount between about 0.01% to about 5% (by total weight of the composition), or in some embodiments between about 0.05 to about 3% (by total weight of the composition).

Preservatives

The anti-adherent compositions may include various preservatives to increase shelf life. Some suitable preservatives that may be used in the present disclosure include, but are not limited to phenoxyethanol, capryl glycol, glyceryl caprylate, sorbic acid, gallic acid, KATHON CG®, which is a mixture of methylchloroisothiazolinone and methylisothiazolinone, (available from Rohm & Haas Company, Philadelphia, Pa.); DMDM hydantoin (e.g., GLYDANT, available from Lonza, Inc., Fair Lawn, N.J.); EDTA and salts thereof; iodopropynyl butylcarbamate; benzoic esters (parabens), such as methylparaben, propylparaben, butylparaben, ethylparaben, isopropylparaben, isobutylparaben, benzylparaben, sodium methylparaben, and sodium propylparaben; 2-bromo-2-nitropropane-1,3-diol; benzoic acid; and the like. Other suitable preservatives include those sold by Sutton Labs Inc., Chatham, N.J., such as "GERMALL 115" (imidazolidinyl urea), "GERMALL II" (diazolidinyl urea), and "GERMALL PLUS" (diazolidinyl urea and iodopropynyl butylcarbonate).

The amount of the preservative in the anti-adherent compositions is dependent on the relative amounts of other components present within the composition. For example, in some embodiments, the preservative is present in the compositions in an amount between about 0.001% to about 5% (by total weight of the composition), in some embodiments between about 0.01 to about 3% (by total weight of the composition), and in some embodiments, between about 0.05% to about 1.0% (by total weight of the composition).

Preparation of Anti-Adherent Compositions

The anti-adherent compositions of the present disclosure may be prepared by combining ingredients at room temperature and mixing.

In one embodiment, when the anti-adherent composition is to be applied to the skin of an individual, the composition includes the anti-adherent agent, a hydrophilic carrier and a hydrophilic thickener. Suitable hydrophilic carriers can be, for example, water, glycerin, glycerin derivatives, glycols, water-soluble emollients, and combinations thereof. Suitable examples of glycerin derivatives could include, but are not to be limited to, PEG-7 glyceryl cocoate. Suitable glycols could include, but are not to be limited to, propylene glycol, butylene glycol, pentylene glycol, ethoxydiglycol, dipropylene glycol, propanediol, and PEG-8. Suitable examples of water-soluble emollients could include, but are not to be limited to, PEG-6 Caprylic Capric Glycerides, Hydrolyzed Jojoba Esters, and PEG-10 Sunflower Glycerides.

Delivery Vehicles

The anti-adherent compositions of the present disclosure may be used in combination with a product. For example, the composition may be incorporated into or onto a substrate, such as a wipe substrate, an absorbent substrate, a fabric or cloth substrate, a tissue substrate, or the like. In one embodiment, the anti-adherent composition may be used in combination with a wipe substrate to form a wet wipe or may be a wetting composition for use in combination with a wipe which may be dispersible. In other embodiments, the anti-adherent composition may be incorporated into wipes such as wet wipes, hand wipes, face wipes, cosmetic wipes, cloths and the like. In yet other embodiments, the anti-adherent compositions described herein can be used in combination with numerous personal care products, such as absorbent articles. Absorbent articles of interest are diapers, training pants, adult incontinence products, feminine hygiene products, and the like; bath or facial tissue; and paper towels. Personal protective equipment articles of interest include but are not limited to masks, gowns, gloves, caps, and the like.

In one embodiment, the wet wipe may comprise a nonwoven material that is wetted with an aqueous solution termed the "wetting composition," which may include or be composed entirely of the anti-adherent compositions disclosed herein. As used herein, the nonwoven material comprises a fibrous material or substrate, where the fibrous material or substrate comprises a sheet that has a structure of individual fibers or filaments randomly arranged in a mat-like fashion. Nonwoven materials may be made from a variety of processes including, but not limited to, airlaid processes, wet-laid processes such as with cellulosic-based tissues or towels, hydroentangling processes, staple fiber carding and bonding, melt blown, and solution spinning.

The fibers forming the fibrous material may be made from a variety of materials including natural fibers, synthetic fibers, and combinations thereof. The choice of fibers may depend upon, for example, the intended end use of the finished substrate and the fiber cost. For instance, suitable fibers may include, but are not limited to, natural fibers such as cotton, linen, jute, hemp, wool, wood pulp, etc. Similarly, suitable fibers may also include: regenerated cellulosic fibers, such as viscose rayon and cuprammonium rayon; modified cellulosic fibers, such as cellulose acetate; or synthetic fibers, such as those derived from polypropylenes, polyethylenes, polyolefins, polyesters, polyamides, polyacrylics, etc. Regenerated cellulose fibers, as briefly discussed above, include rayon in all its varieties as well as other fibers derived from viscose or chemically modified cellulose, including regenerated cellulose and solvent-spun cellulose, such as Lyocell. Among wood pulp fibers, any known papermaking fibers may be used, including softwood and hardwood fibers. Fibers, for example, may be chemically pulped or mechanically pulped, bleached or unbleached, virgin or recycled, high yield or low yield, and the like. Chemically treated natural cellulosic fibers may be used, such as mercerized pulps, chemically stiffened or crosslinked fibers, or sulfonated fibers.

In addition, cellulose produced by microbes and other cellulosic derivatives may be used. As used herein, the term "cellulosic" is meant to include any material having cellulose as a major constituent, and, specifically, comprising at least 50 percent by weight cellulose or a cellulose derivative. Thus, the term includes cotton, typical wood pulps, non-woody cellulosic fibers, cellulose acetate, cellulose triacetate, rayon, thermomechanical wood pulp, chemical wood pulp, debonded chemical wood pulp, milkweed, or bacterial cellulose. Blends of one or more of any of the previously described fibers may also be used, if so desired.

The fibrous material may be formed from a single layer or multiple layers. In the case of multiple layers, the layers are generally positioned in a juxtaposed or surface-to-surface relationship and all or a portion of the layers may be bound to adjacent layers. The fibrous material may also be formed from a plurality of separate fibrous materials wherein each of the separate fibrous materials may be formed from a different type of fiber.

Airlaid nonwoven fabrics are particularly well suited for use as wet wipes. The basis weights for airlaid nonwoven fabrics may range from about 20 to about 200 grams per square meter (gsm) with staple fibers having a denier of about 0.5 to about 10 and a length of about 6 to about 15 millimeters. Wet wipes may generally have a fiber density of about 0.025 g/cc to about 0.2 g/cc. Wet wipes may generally have a basis weight of about 20 gsm to about 150 gsm. More desirably the basis weight may be from about 30 to about 90 gsm. Even more desirably the basis weight may be from about 50 gsm to about 75 gsm.

Processes for producing airlaid non-woven basesheets are described in, for example, published U.S. Pat. App. No. 2006/0008621, herein incorporated by reference to the extent it is consistent herewith.

The disclosure will be more fully understood upon consideration of the following non-limiting Examples.

EXAMPLES

Example 1

The anti-adherent agents affect bacterial adherence to MBEC polystyrene pegs (see explanation below) in three different ways: 1) anti-adherent agents have a greater than or equal to 1 Log reduction of bacteria to the pegs, 2) neutral compounds have between 0.9 Log reduction of bacteria to the pegs and 0.9 Log increase of bacteria on the pegs, 3) adherent agents have a greater than or equal to 1 Log increase of bacteria on the pegs. No agents with anti-adherent activity were found to be antimicrobial (data not shown). In this example, anti-adherent agents of the present disclosure were tested using the High Throughput Anti-adherence Test Method or the VIABLE COUNT ANTI-ADHERENCE TEST METHOD, infra, against Gram-positive *Staphylococcus aureus*. The anti-adherent agents are shown in Table 2 below.

The pH of the anti-adherent composition is between 3 to 10 pH, or about 4 to about 8 pH.

TABLE 2

Anti-adherent Agents and Corresponding Log Reduction of *S. aureus*

| Agent | Con. Wt. % | INCI | Average Log reduction *S. aureus* ATCC** 6538 |
|---|---|---|---|
| ABIL B 9950 | 5 | Dimethicone Propyl PG-Betaine | 2.2 |
| ACULYN 44 | 1 | PEG-150/Decyl Alcohol/SMDI Copolymer | 1.7 |
| ARISTOFLEX TAC | 0.5 | Ammonium Acryloyl Dimethyltaurate/Carboxyethyl Acrylate Crosspolymer | 2.0 |
| BARNET BPS 20 | 3 | Peg-20 Soy Sterol | 2.3 |
| BELSIL 6031 | 5 | PEG/PPG-25/25 Dimethicone | 2.3 |
| DC 193 | 5 | PEG-12 dimethicone | 2.3 |
| DC 200 (100 CST) | 100 | Dimethicone | 1.8 |
| DC 9011 | 100 | Cyclopentasiloxane (and) PEG-12 Dimethicone Crosspolymer | 1.9 |
| LANEXOL AWS | 5 | PPG-12-PEG-50 Lanolin | 2.6 |
| LYSOFIX | 5 | Glycerin (and) *Glycine Max* (Soybean) Seed Extract | 2.4 |
| PECOGEL S1120 | 3 | VP/Dimethiconylacrylate/Polycarbamyl/Polyglycol Ester | 1.7 |
| FLORASOLVS PEG-10 Sunflower | 3.50 | PEG-10 Sunflower Glycerides | 2.4 |
| SILAMINE C300 | 5 | PEG-8 Amodimethicone | 1.7 |
| SILSOFT 440 | 5 | PEG/PPG 20/23 Dimethicone | 1.4 |

For all samples tested, the final pH was between 5 and 7.5 unless otherwise noted.
**"ATCC" is the acronym for the American Type Culture Collection, Manassas, VA
Con. Wt. % = Concentration of Agent in 5% glycerin and water, by total weight of solution, percent

TABLE 3

Anti-adherent Agents and Corresponding Log Reduction of *S. aureus* using the Viable Count Anti-Adherence Test Method

| AGENT | Con. Wt. % | INCI | Average Log reduction S. aureus ATCC** 6538 |
|---|---|---|---|
| AQUA FLEX FX-64 | 5 | Isobutylene/Ethylmaleimide/Hydroxyethylmaleimide Copolymer | 0.68 |
| DIAFORMER Z-301N | 5 | Methacryloyl Ethyl Betaine/Acrylates Copolymer | 0.81 |
| PLURONIC F 127 | 5 | Poloxamer 407 | 1.15 |
| PLURONIC L105 | 5 | Unknown | 1.34 |
| POLYDERM PPI-CO-200 | 5 | PEG-200 Hydrogenated Castor Oil/IPDI Copolymer | 1.01 |
| POLYNECON PPI-SA-15D | 5 | PEG-15 Soyamine/IPDI Copolymer Dimer Dilinoleate | 1.29 |
| SILSENSE DW-18 SILICONE | 5 | Dimethicone PEG-7 Isostearate | 0.91 |
| SILSOFT 875 | 5 | PEG-12 Dimethicone | 1.46 |
| SILSOFT 895 | 5 | PEG-17 Dimethicone | 1.29 |
| UCON TPEG-500 | 2.5 | Polyoxyethylene Polyoxypropylene block copolymer | 0.54 |
| NUWET 237 | 5 | Polyalkyleneoxide modified silicone copolymer | 0.78 |
| DERMOTHIX 75 LIQUID | 5 | Disteareth-75 IPDI | 0.54 |

For all samples tested, the final pH was between 5 and 7.5 unless otherwise noted.
**"ATCC" is the acronym for the American Type Culture Collection, Manassas, VA
Con. Wt. % = Concentration of Agent in 5% glycerin and water, by total weight of solution, percent Test Methods High Throughput Anti-Adherence Test Method This test method specifies the operational parameters required to grow and or prevent the formation of bacterial attachment using a high throughput screening assay. The assay device consists of a plastic lid with ninety-six (96) pegs and a corresponding receiver plate with ninety-six (96) individual wells that have a maximum 200 μL working volume. Biofilm is established on the pegs under static batch conditions (i.e., no flow of nutrients into or out of an individual well).
1. Terminology
    1.2 Definitions of Terms Specific to This Standard:
        1.2.2 peg, n—biofilm sample surface (base: 5.0 mm, height: 13.1 mm).
        1.2.3 peg lid, n—an 86×128 mm plastic surface consisting of ninety-six (96) identical pegs.
        1.2.4 plate, n—an 86×128 mm standard plate consisting of ninety-six (96) identical wells.
        1.2.5 well, n—small reservoir with a 50 to 200 μL working volume capacity.
2. Acronyms
    2.2 ATCC: American Type Culture Collection
    2.3 CFU: colony forming unit
    2.4 rpm: revolutions per minute
    2.5 SC: sterility control
    2.6 TSA: tryptic soy agar
    2.7 TSB: tryptic soy broth
    2.8 GC: growth control
3. Apparatus
    3.2 Inoculating loop—nichrome wire or disposable plastic.
    3.3 Petri dish—large labelled (100×150×15 mm, plastic, sterile) for plating.
    3.4 Microcentrifuge tubes—sterile, any with a 1.5 mL volume capacity.
    3.5 96-well microtiter plate—sterile, 86×128 mm standard plate consisting of ninety-six (96) identical flat bottom wells with a 200 μL working volume
    3.6 Vortex—any vortex that will ensure proper agitation and mixing of microfuge tubes.
    3.7 Pipette—continuously adjustable pipette with volume capability of 1 mL.
    3.8 Micropipette—continuously adjustable pipette with working volume of 10 μL-200 μL.
    3.9 Sterile pipette tips—200 uL and 1000 uL volumes.
    3.10 Sterile reagent reservoir—50 mL polystyrene.
    3.11 Sterilizer—any steam sterilizer capable of producing the conditions of sterilization.
    3.12 Colony counter—any one of several types may be used. A hand tally for the recording of the bacterial count is recommended if manual counting is done.
    3.13 Environmental incubator—capable of maintaining a temperature of 35±2° C. and relative humidity between 35 and 85%.
    3.14 Reactor components—the MBEC Assay device available from Innovotech, Edmonton, AB, Canada.
    3.15 Sterile conical tubes—50 mL, used to prepare initial inoculum.
    3.16 Appropriate glassware—as required to make media and agar plates.
    3.17 Erlenmeyer flask—used for growing broth inoculum.
    3.18 Positive Displacement pipettes capable of pipetting 200 μL.
    3.19 Sterile pipette tips appropriate for Positive Displacement pipettes.
4. Reagents and Materials
    4.2 Purity of water—all references to water as diluent or reagent shall mean distilled water or water of equal purity.

4.3 Culture media:
4.4 Bacterial growth broth—Tryptic soy broth (TSB) prepared according to manufacturer's directions.
4.5 Bacterial plating medium—Tryptic soy agar (TSA) prepared according to manufacturer's directions.
4.6 Phosphate Buffered Saline (PBS)—
4.7 Rinse Solution: Sterile PBS and TWEEN 80 (Sigma-Aldrich, St. Louis, Mo.) 1% w/v.

5. MICROORGANISM:
   5.1 *S. aureus* ATCC 6538
6. TEST METHOD overview: The experimental process for the High-Throughput Anti-Adherence Test Method. This standard protocol may be broken into a series of small steps, each of which is detailed in the sections below.
   6.1 Culture Preparation
      6.1.1 *S. aureus* ATCC 6538 are the organisms used in this test.
      6.1.2 Using a cryogenic stock (at −70° C.), streak out a subculture of the above listed microorganisms on organism's specific agar (TSA).
      6.1.3 Incubate at 35±2° C. for the period of time of 22±2 hours.
      6.1.4 9.1.4 Aseptically remove isolated colony from streak plate and inoculate 20 mL of sterile TSB.
      6.1.5 Incubate flask at 35±2° C. and 175±10 rpm for 16 to 18 hours (*S. aureus*). Viable bacterial density should be $10^9$ CFU/mL and should be checked by serial dilution and plating.
      6.1.6 Pipette 10 mL from the incubation flask of *S. aureus* into a 50 mL conical tube and spin down at 5 minutes at 4,000×g. Then remove supernatant and resuspend in 10 mL sterile PBS. Approximate cell density should be $10^7$-$10^9$ CFU/mL. Vortex the sample for approximately 30 seconds to achieve a homogeneous distribution of cells.
      6.1.7 Perform 10-fold serial dilutions of the inoculum in triplicate.
      6.1.8 Plate appropriate dilutions on appropriately labelled TSA plates. Incubate the plates at 35±2° C. for 22±2 hours depending on the isolates growth rate and enumerate.
   6.2 Preparation of the Challenge plates:
      6.2.1 Preparation of compounds and coating compounds onto MBEC plate lid
         6.2.1.1.1 Using a positive displacement pipette aseptically add 200 μL of compounds and control to be tested to a sterile 96-well microplate according to the plate layout of Table 4.
         6.2.1.1.2 Add 200 μL of each code to the appropriate well for sterility controls.
         6.2.1.1.3 Place the MBEC plate lid, peg side down into the 96-well microplate containing the test compound solutions.
         6.2.1.1.4 Allow the plate to sit at room temperature (25±3° C.) for 2 hours.
         6.2.1.1.5 Remove the MBEC plate lid and allow the lid to dry at room temperature (25±3° C.) overnight in a laminar flow hood.
   7.1 Bacterial Adherence Challenge:
      7.1.1 Add 100 μL of diluted bacteria to the appropriate wells in a sterile 96-well microplate as indicated in the plate layout in Table 4.
      7.1.2 Add 200 μL of sterile PBS to the sterility controls.
      7.1.3 The MBEC containing dried compounds is then inserted into the bacterial inoculated 96 well flat bottom microplate from section 9.3.1
      7.1.4 Incubate stationary at room temperature (25±3° C.) for 15 minutes.
      7.1.5 Remove the MBEC lid and place into a 96-well microplate containing 200 μL PBS+1% w/v TWEEN 80. Incubate stationary at room temperature (25±3° C.) for 15 seconds.
      7.1.6 Repeat step 7.1.5 for two additional washes for a total of 3 washes.
   7.2 Method to Determine Number of Attached Bacteria
      7.2.1 Transfer the washed MBEC plate lid to a 96-well plate containing 200 μL ALAMARBLUE reagent (prepared according to manufacturer's directions, Life Technologies, Carlsbad, Calif.) in each well to be tested.
      7.2.2 The final plate is transferred to a SPECTRAMAX GEMINI EM microplate reader (Molecular Devices, Inc. Sunnyvale, Calif. USA) for a 20 hour kinetic, bottom read with an excitation of 560 nm and emission of 590 nm. The rate of fluorescence development (relative fluorescence units (RFU)/minute) is determined for each well.
      7.2.3 Data was analyzed using a standard curve (described below) for each organism to determine the numbers of bacteria attached to the pegs (Log 10 CFU/mL) present in each sample. Number of attached bacteria was quantified by incubating with an ALAMARBLUE reagent and measuring fluorescence development over time.
      7.2.4 From these data, the Log 10 CFU/mL reduction of each time point relative to the growth control is calculated to determine the activity of each code.

TABLE 4

Sample layout of 96-well MBEC plate.

|  |  | 1 | 2 | 3 | 4 | 5 | 6 | 7 | 8 | 9 | 10 | 11 | 12 |
|---|---|---|---|---|---|---|---|---|---|---|---|---|---|
| *S. aureus* | A | AAC |  | T1 | T2 | T3 | T4 | T5 | T6 | T7 | T8 | NT-GC | T1-SC |
| *S. aureus* | B | AAC |  | T1 | T2 | T3 | T4 | T5 | T6 | T7 | T8 | NT-GC | T2-SC |
| *S. aureus* | C | AAC |  | T1 | T2 | T3 | T4 | T5 | T6 | T7 | T8 | NT-GC | T3-SC |
| *S. aureus* | D | AAC |  | T1 | T2 | T3 | T4 | T5 | T6 | T7 | T8 | NT-GC | T4-SC |
| *S. aureus* | E | AAC |  | T1 | T2 | T3 | T4 | T5 | T6 | T7 | T8 | NT-GC | T5-SC |
| *S. aureus* | F | AAC |  | T1 | T2 | T3 | T4 | T5 | T6 | T7 | T8 | NT-GC | T6-SC |
| *S. aureus* | G | AAC |  | T1 | T2 | T3 | T4 | T5 | T6 | T7 | T8 | NT-GC | T7-SC |
| *S. aureus* | H | AAC |  | T1 | T2 | T3 | T4 | T5 | T6 | T7 | T8 | NT-GC | T8-SC |

AAC = Anti-Adherent Control
SC = Sterility Control
NT-GC = No Treatment Growth Control
T1-T8 = Test Codes 7.3 Method for Generating a Standard Curve with bacteria in an ALAMARBLUE Solution:
- 7.3.1 Standard curves were constructed for each organism to define the rate of fluorescence development as a function of bacterial concentration, as determined via viable plate counts. This standard curve provided the ability to relate rate of fluorescence development (RFU/minute) to the Log 10 CFU/mL number of bacteria present in a given sample
- 7.3.2 Day 1:
  - 7.3.2.1 Aseptically remove loopful of bacteria strain to be tested from freezer stock and place in 20 mL of TSB media in a culture flask.
  - 7.3.2.2 Incubate with shaking (200 rpm) for 22±2 hours at 37±2° C.
- 7.3.3 Day 2:
  - 7.3.3.1 Aseptically transfer 100 µL of the 22±2 hours freezer stock cultures into 20 mL of TSB media in a culture flask.
  - 7.3.3.2 Incubate cultures on a gyrorotary shaker (200 rpm) for 22±2 hours at 37±2° C.
  - 7.3.3.3 Perform a streak for isolation from the culture flask on TSA. Incubate plate for 22±2 hours at 37±2° C.
- 7.3.4 Day 3:
  - 7.3.4.1 Prepare an ALAMARBLUE solution according to the manufacturer's directions.
  - 7.3.4.2 Remove culture flask from shaking incubator after 22±2 hours. Pipette 1 mL of bacteria into a 1.7 mL microcentrifuge tube.
  - 7.3.4.3 Centrifuge the bacteria at 4000×g.
  - 7.3.4.4 Resuspend bacterial cells in sterile PBS. Perform a total of two washes.
  - 7.3.4.5 Perform 1:10 serial dilutions with washed bacterial culture in 0.9 mL dilution blanks of sterile PBS (100 µL culture into 900 µL of sterile PBS).
  - 7.3.4.6 Plate appropriate dilutions of prepared bacteria.
  - 7.3.4.7 Add 270 µL of ALAMARBLUE solution to wells A-D: columns 1-7 of a 96-well plate.
  - 7.3.4.8 Add 30 µL of bacterial dilution the wells of a 96-well plate (n=4 per dilution).
  - 7.3.4.9 Add 30 µL of sterile PBS to wells A-D, column 8 for a background control.
  - 7.3.4.10 Place plate in a bottom reading spectrophotometer that measures fluorescence. Set temp to 37° C. Perform assay at 37° C., read every 20 minutes for 24 hours at 560 excite and 590 emit.
  - 7.3.4.11 Enumerate the dilutions.
  - 7.3.4.12 Calculate the mean rate of fluorescence development.
  - 7.3.4.13 Plot the mean rate of fluorescence development as a function of the mean CFU/mL of the dilutions.

Viable Count Anti-Adherence Test Method

This test method specifies the operational parameters required to grow and or prevent the formation of bacterial attachment using viable counts. The assay device consists of a plastic lid with ninety-six (96) pegs and a corresponding receiver plate with ninety-six (96) individual wells that have a maximum 200 µL working volume. Biofilm is established on the pegs under static batch conditions (i.e., no flow of nutrients into or out of an individual well).

This test method is identical to the High Throughput Anti-Adherence Test Method except that Section 7.1 through 7.3.4.13 is replaced with the following:

A. Bacterial Adherence Challenge:
  - A.1 Add 100 µL of diluted bacteria to the appropriate wells in a sterile 96-well microplate as indicated in the plate layout in Table 4.
  - A.2 Add 200 µL of sterile PBS to the sterility controls.
  - A.3 The MBEC containing dried compounds is then inserted into the bacterial inoculated 96 well flat bottom microplate from section 9.3.1
B. Recovery:
  - B.1 After the 15 minute contact time, transfer the MBEC™ lid to the rinse plate where each well contains 200 µL for 15 seconds of saline and 1% Tween 80 to wash of any loosely attached planktonic cells. Repeat this for 3 separate wash plates.
  - B.2 *S. aureus* Recovery:
    - B.2.1 Break the corresponding pegs from the MBEC™ lid using a sterile pliers and transfer them into 50 mL conical tubes containing 10 mL PBS.
    - B.2.2 Vortex the conical tubes for 10 seconds
    - B.2.3 Transfer the conical tubes to the sonicator and sonicate on high. Sonicate for 1 minute on. Then allow the tubes to rest for 1 minute. Repeat the sonication step for a total of 5 minutes of sonication to dislodge surviving attached bacteria. The conical tubes were placed in the sonicator water bath using a float.
    - B.2.4 Vortex the conical tubes again for 10 seconds.
  - B.3 *E. coli* Recovery:
    - B.3.1 Transfer the MBECTM lid to a plate containing 200 µL PBS.
    - B.3.2 Transfer the plate to the sonicator and sonicate on high for 10 minutes to dislodge surviving attached bacteria. The plates are placed in a dry stainless steel insert tray which sits in the water of the sonicator. The vibrations created in the water by the sonicator transfer through the insert tray to actively sonicate the contents of the 96 well recovery plate(s).
C. $LOG_{10}$ Reduction:
  - C.1 Following sonication, place 100 µL from each well of the MBEC™ plate, into the first 12 empty wells of the first row of a 96 well-micro titer plate. Place 180 µL of sterile 0.9% saline in the remaining rows.
  - C.2 Prepare a serial dilution ($10^0$-$10^{-7}$) by moving 20 µL down each of the 8 rows.
  - C.3 Remove 10 µL from each well and spot plate on a prepared TSA plates.
  - C.4 Plates are incubated at 37±1° C. and counted after approximately 24 h hours of incubation.
  - C.5 Data will be evaluated as Log10 CFU/peg.
  - C.6 Cell Enumeration:
  - C.7 Count the appropriate number of colonies according to the plating method used.
  - C.8 Calculate the arithmetic mean of the colonies counted on the plates.
    - C.8.1 The log density for one peg is calculated as follows:

$Log_{10}(CFU/peg)=Log_{10}[(X/B)(D)]$ where:

X=mean CFU; B=volume plated (0.02 mL); and D=dilution.

- C.9 Calculate the overall attached bacteria accumulation by calculating the mean of the log densities calculated.
  - C.10 Calculate the Logic) reduction for each dilution as follows: LOG10 Reduction=Mean $LOG_{10}$ Growth Control–Mean $Log_{10}$ Test.

Explanation of Log Decrease

The compositions of the present disclosure exhibit a decrease of bacteria on surfaces. Log decrease, for example, may be determined from the decrease of bacteria adhered to a surface according to the following correlations:

| Fold Decrease of Bacteria | LOG Decrease |
|---|---|
| 1 | 0.5 |
| 10 | 1 |
| 100 | 2 |
| 1000 | 3 |

In other words, surface exhibiting a decrease of bacteria of 1 Log means the number of bacteria on the fibrous substrate has decreased 10-fold, a decrease of 2 Log means the number of bacteria has decreased 100-fold, a decrease of 3 Log means the number of bacteria has decreased 1000-fold, etc., as compared to the number of bacteria present on a surface that is not treated with the disclosed composition. A larger Log decrease thus corresponds with a composition that is able to more effectively repel Gram negative and Gram positive bacteria.

When introducing elements of the present disclosure, the articles "a", "an", "the" and "said" are intended to mean that there are one or more of the elements. The terms "comprising", "including" and "having" are intended to be inclusive and mean that there may be additional elements other than the listed elements. Many modifications and variations of the present disclosure can be made without departing from the spirit and scope thereof. Therefore, the exemplary embodiments described above should not be used to limit the scope of the disclosure.

What is claimed is:

1. A non-antimicrobial composition for inhibiting the attachment of microbes to a surface, the non-antimicrobial composition comprising:
   a liquid carrier; and
   an effective amount of an anti-adherent agent selected from the group consisting of Dimethicone Propyl PG-Betaine, PEG-150/Decyl Alcohol/SMDI Copolymer, Ammonium Acryloyl Dimethyltaurate/Carboxyethyl Acrylate Crosspolymer, PEG-20 Soy Sterol, PEG/PPG-25/25 Dimethicone, PPG-12-PEG-50 Lanolin, Glycerin (and) Glycine Max (Soybean) Seed Extract, VP/Dimethiconylacrylate/Polycarbamyl/Polyglycol Ester, PEG-10 Sunflower Glycerides, PEG-8 Amodimethicone, PEG/PPG 20/23 Dimethicone, Methacryloyl Ethyl Betaine/Acrylates Copolymer, PEG-200 Hydrogenated Castor Oil/IPDI Copolymer, PEG-15 Soyamine/IPDI Copolymer Dimer Dilinoleate, PEG-17 Dimethicone, and combinations thereof; and
   wherein the anti-adherent agent is a non-antimicrobial and is present in the amount of 0.10% to 20% by weight of the composition.

2. The composition of claim 1 wherein the liquid carrier is hydrophilic.

3. The composition of 1 further comprising a humectant selected from the group consisting of glycerin, glycerin derivatives, hyaluronic acid derivatives, betaine derivatives amino acids, amino acid derivatives, glycosaminoglycans, glycols, polyols, sugars, sugar alcohols, hydrogenated starch hydrolysates, hydroxy acids, hydroxy acid derivatives, salts of PCA, and combinations thereof.

4. The composition of claim 1 further comprising a humectant selected from the group consisting of honey, sorbitol, hyaluronic acid, sodium hyaluronate, betaine, lactic acid, citric acid, sodium citrate, glycolic acid, sodium glycolate, sodium lactate, urea, propylene glycol, butylene glycol, pentylene glycol, ethoxydiglycol, methyl gluceth-10, methyl gluceth-20, PEG-2, PEG-4, PEG-5, PEG-6, PEG-7, PEG-8, PEG-9, PEG-10, Propanediol, xylitol, maltitol, and combinations thereof.

5. The composition of claim 1 comprising an emollient.

6. The composition of claim 1 further comprising an emulsifier.

7. The composition of claim 1 wherein the anti-adherent agent reduces the attachment of microbes to a polystyrene surface by at least 0.5 Log of bacteria according to a High Throughput Anti-adherent Test or a Viable Count Anti-adherence Test Method.

8. The composition of claim 1 wherein the anti-adherent agent reduces the attachment of microbes to a polystyrene surface by at least 1 Log of bacteria according to a High Throughput Anti-adherent Test or a Viable Count Anti-adherence Test Method.

9. The composition of claim 1 further comprising a foaming agent.

10. A wipe comprising:
    a nonwoven substrate;
    an anti-adherent agent composition comprising 0.10% to 20% by total weight of composition of an anti-adherent agent; and
    a hydrophilic carrier;
    wherein the composition reduces the adherence of S. aureus on a surface by at least 0.5 log according to a High Throughput Anti-adherent Test Method or a Viable Count Anti-adherence Test Method, and
    wherein the anti-adherent composition is non-antimicrobial and the anti-adherent agent is selected from the group consisting of Dimethicone Propyl PG-Betaine, PEG-150/Decyl Alcohol/SMDI Copolymer, Ammonium Acryloyl Dimethyltaurate/Carboxyethyl Acrylate Crosspolymer, PEG-20 Soy Sterol, PEG/PPG-25/25 Dimethicone, PPG-12-PEG-50 Lanolin, Glycerin (and) Glycine Max (Soybean) Seed Extract, VP/Dimethiconylacrylate/Polycarbamyl/Polyglycol Ester, PEG-10 Sunflower Glycerides, PEG-8 Amodimethicone, PEG/PPG 20/23 Dimethicone, Methacryloyl Ethyl Betaine/Acrylates Copolymer, PEG-200 Hydrogenated Castor Oil/IPDI Copolymer, PEG-15 Soyamine/IPDI Copolymer Dimer Dilinoleate, PEG-17 Dimethicone, and combinations thereof.

11. The wipe of claim 10 wherein the anti-adherent agent is present in the amount of 0.1% to 10% by total weight of the composition.

12. The wipe of claim 10 wherein the anti-adherent composition further comprises one or more of ingredients selected from the group consisting of a humectant, an emollient, an emulsifier, and any combination thereof.

* * * * *